(12) United States Patent
Stapleford

(10) Patent No.: US 9,153,119 B2
(45) Date of Patent: Oct. 6, 2015

(54) SCENTING NEBULIZER WITH REMOTE MANAGEMENT AND CAPACITIVE LIQUID LEVEL SENSING

(71) Applicant: Scott Stapleford, Londonderry, NH (US)

(72) Inventor: Scott Stapleford, Londonderry, NH (US)

( * ) Notice: Subject to any disclaimer, the term of this patent is extended or adjusted under 35 U.S.C. 154(b) by 0 days.

(21) Appl. No.: 14/705,008

(22) Filed: May 6, 2015

(65) Prior Publication Data

US 2015/0235546 A1    Aug. 20, 2015

Related U.S. Application Data

(60) Provisional application No. 62/151,529, filed on Apr. 23, 2015.

(51) Int. Cl.
  *G01F 23/26* (2006.01)
  *G08B 21/18* (2006.01)

(52) U.S. Cl.
  CPC ............ *G08B 21/182* (2013.01); *G01F 23/266* (2013.01); *G01F 23/268* (2013.01)

(58) Field of Classification Search
  CPC ... G01F 23/263; G01F 23/265; G01F 23/266; G01F 23/268; G08B 21/182
  See application file for complete search history.

(56) References Cited

U.S. PATENT DOCUMENTS

| | | | | |
|---|---|---|---|---|
| 5,477,727 | A * | 12/1995 | Koga | 73/304 C |
| 5,726,908 | A * | 3/1998 | Hosmer et al. | 702/55 |
| 7,509,856 | B1 * | 3/2009 | Winkens et al. | 73/304 C |
| 2003/0000303 | A1 * | 1/2003 | Livingston et al. | 73/304 C |
| 2005/0045621 | A1 * | 3/2005 | Chenier et al. | 219/490 |
| 2009/0031798 | A1 * | 2/2009 | Radhakrishnan et al. | 73/304 C |
| 2009/0158841 | A1 * | 6/2009 | Winkens | 73/304 C |
| 2009/0187357 | A1 * | 7/2009 | Ho et al. | 702/52 |
| 2010/0154534 | A1 * | 6/2010 | Hampton | 73/304 C |
| 2010/0253371 | A1 * | 10/2010 | Bierl et al. | 324/698 |
| 2011/0265562 | A1 * | 11/2011 | Li | 73/304 C |
| 2011/0314907 | A1 * | 12/2011 | Wiedekind-Klein | 73/304 C |
| 2012/0065904 | A1 * | 3/2012 | Tichborne et al. | 702/55 |
| 2012/0298157 | A1 * | 11/2012 | Noh et al. | 134/57 R |
| 2014/0191054 | A1 * | 7/2014 | Hingley et al. | 239/1 |

* cited by examiner

*Primary Examiner* — Brian Zimmerman
*Assistant Examiner* — An T Nguyen
(74) *Attorney, Agent, or Firm* — Joseph E. Funk

(57) ABSTRACT

A scenting nebulizer is described that capacitively measures the level of scenting oil in a bottle in the nebulizer without ever contacting the oil in the bottle. In addition, such capacitively measured oil levels are measured at multiple vertical levels of the bottle of scenting oil. In actual operation the capacitively measured oil level readings are very frequently measured then averaged, and the averaged figures are stored. The stored, averaged figures are interpolated against previously stored, capacitance readings made when the scenting oil bottle is full and when there is no bottle. In this manner the level of the oil is accurately determined. A plurality of processor controlled scenting nebulizers are connected to a central computer and their individual oil levels and other operational information are forwarded to the central computer where appropriate maintenance for the individual nebulizers is scheduled. The operational settings operation of the nebulizers may be programmed from the central computer.

5 Claims, 7 Drawing Sheets

SCENTING NEBULIZER WITH REMOTE MANAGEMENT AND CAPACITIVE LIQUID LEVEL SENSING

RELATED APPLICATIONS

This application claims the benefit of U.S. Provisional Application 62/151,529 filed Apr. 23, 2015, which is incorporated herein in its entirety by reference.

FIELD OF THE INVENTION

The invention relates to electronic liquid level sensors and, particularly, to a capacitive liquid level sensor that is functioning with a local microprocessor both used in a scenting nebulizer to monitor the level of scenting oil in a container inside the nebulizer in a way that does not physically contact the oil. The invention also relates to a centralized computer that monitors the operation of and the level of scenting oil in each of a plurality of remote scenting nebulizers and provides a warning signal when a problem is detected and/or the capacitive liquid level sensors of the nebulizers detect that the level of scenting oil in the nebulizer is low. The centralized computer also monitors the operating settings of the nebulizers and is used to program their operational settings.

More specifically, the capacitive liquid level sensor of the invention is utilized in a scenting nebulizer used in a public environment where "scenting" is used to attract consumers into a retail location or to promote the sale of specific products. The scenting can also be used in a professional environment in waiting rooms to calm patients or to neutralize odors.

BACKGROUND OF THE INVENTION

Currently most public and professional establishments that utilize a scenting nebulizer have no remote management of the nebulizer operational settings or an easy way to check scenting oil levels in the nebulizer. In addition, most of these scenting nebulizers are mounted in hard to reach places, for example, near or inside an HVAC system or high on shelves or in ceilings. Scenting oil levels can get low and run out which causes a support issue where the end-user believes the system is broken; and an intended use issue where the scenting nebulizer is not scenting creating a negative revenue generating environment.

Locations that utilize multiple scenting nebulizers that want to maintain consistency in the times the scenting nebulizers are turned on or off, or to verify all units are functioning correctly or at pre-programmed levels is not achievable with current scenting nebulizers presently available on the market with one exception. U.S. Pat. No. 5,563,811 teaches a system controller interfacing with a number of remote nebulizing humidifiers that allows operator control of the humidifiers via a human interface comprising a keypad and a liquid crystal display. The system controller, operating under control of a program, monitors the operational status of each humidifier and alarms the user on a humidifier fault. The system controller also receives a humidity control signal which monitors the humidity in a particular location or zone using humidity sensors. The system controller sends signals to individual nebulizing humidifiers to control their operation and correct the humidity levels.

What is needed in the art is means to periodically measure the level or amount of scenting oil in each scenting nebulizer, without physically contacting the scenting oil therein, and automatically report the level of oil back to a central location so that oil may replenished before it runs out.

What is also needed in the art is a scenting nebulizer, a number of which may be combined into a networked system, even with nebulizers being in locations remote from each other, and all the nebulizers are under the control of a central processor which monitors their operation for improved maintenance services. This includes monitoring the level of scenting oil in each remote nebulizer and causing the oil in a nebulizer to be replenished when the oil level is low.

SUMMARY OF THE INVENTION

The previously described needs in the prior art are satisfied by the present invention. In a preferred embodiment of the invention described herein a scenting nebulizer is provided which has a microprocessor controlled scenting oil pump and a scenting oil level detection means that does not physically contact the oil in the nebulizer. This aspect of the invention may be used to monitor liquid levels other than in a nebulizer. This no contact scenting oil level monitoring eliminates fouling of such oil level measuring means in the scenting nebulizers and thereby minimizes maintenance services. The scenting nebulizer has keys for inputting commands to the microprocessor to control the operation of the nebulizer and a display for providing visual indications of the operational characteristics of the nebulizer.

More specifically, the no contact oil level detection means is a capacitive oil level measuring means which functions with the microprocessor for periodically monitoring the level of the scenting oil in the nebulizer. The monitoring period can be as little as every few seconds. The scenting nebulizer is supplied scented oil via a replaceable bottle that is attached to the nebulizer. The oil bottle is screwed onto the nebulizing assembly through a front door of the scenting unit which has a clear door for visual check of the oil level.

In addition, a programmed central computer is provided that monitors and controls the operation of each of a plurality of networked scenting nebulizers, that may remotely located from each other, by communicating with the local microprocessors in each of the individual nebulizers. The central computer provides a warning signal when either a problem with a nebulizer is detected and reported by a local microprocessor to the central computer, and/or the capacitive liquid level sensor in the nebulizer detects that the level of scenting oil in the nebulizer is low and that condition is reported by the local microprocessor to the central computer. The central computer may also be used to program the operational settings of individual scenting nebulizers in the network of nebulizers. This eliminates the need to manually check the amount of scenting oil in each of the networked scenting nebulizers, which task is cumbersome when there are a large number of nebulizers and they are spread out and in relatively hard to reach places.

This centralized and networked operation assures that service providers of a scenting nebulizer service have the ability to control and manage a plurality of scenting nebulizers at a number of physical locations each having one or more scenting nebulizers. By continuously monitoring both the operational status and the scenting oil level of a number of remote scenting nebulizers the service provider can promptly maintain the nebulizers and can establish scenting oil reorder points and properly schedule maintenance that reduces or eliminates out-of-oil conditions.

This centralized and networked operation assures that service providers of a scenting nebulizer service have the ability to control and manage a plurality of scenting nebulizers at a number of physical locations each having one or more scenting nebulizers. By continuously monitoring both the operational status and the scenting oil level of a number of remote scenting nebulizers the service provider can promptly maintain the nebulizers and can establish scenting oil reorder points and properly schedule maintenance that reduces or eliminates out-of-oil conditions.

Communication between the local microprocessor of each of the scenting nebulizers at the same and/or different geographical locations and the central computer is accomplished by using a combination of wired and/or wireless local area networks and/or the Internet for transmitting control signals and monitoring information between the local microprocessor of each nebulizer and the central computer.

Each scenting nebulizer utilizes a novel capacitive oil level sensor that, in conjunction with its local processor, continuously monitors the level of scenting oil in the bottle of oil attached to each nebulizer without physically contacting the scenting oil. This contactless operation prevents any fouling of the oil level sensor over time and thereby minimizes maintenance of the sensor. The level of scenting oil measured by the capacitive oil level sensor in conjunction with the local microprocessor are forwarded by the local microprocessor to the central computer which monitors the scenting oil levels and the operational status of each of the plurality of scenting nebulizers for maintenance purposes. These maintenance purposes include but are not limited to, repairing malfunctions of a scenting nebulizer and replacing the scenting oil in each nebulizer. In the event that a scenting nebulizer is being operated in a standalone mode its microprocessor Local programming of each scenting nebulizer, is performed right at the nebulizer, through a local interface in the form of an integrated LCD display and membrane keypad located on the front of each scenting nebulizer. The display and keypad are used to receive and send information from/to the local microprocessor associated with each scenting nebulizer. This local interface allows for scenting schedules to be manually programmed and activated based upon date and time. Additionally, nebulizer specific on and off scenting intervals, other network settings, and current time and date may also programmed through this local interface without the involvement of the central computer.

As previously mentioned, the monitoring and programming of individual scenting nebulizers located in different physical locations may be accomplished using a remote central computer with signals being transmitted back and forth between the central computer and the networked scenting nebulizers via a wired and/or wireless local area network and/or the Internet. This remote operation permits scenting scheduling changes, date/time updates, updating software in the individual scenting nebulizers, and firmware updates in the individual scenting nebulizers.

The nebulized oil output from a scenting nebulizer can either be input into the air passing through an HVAC system or can be sprayed directly into a room environment. Scenting nebulizers that are connected to an HVAC system are wired to be energized and spray nebulized scenting oil into the airflow only when the HVAC fan is running.

BRIEF DESCRIPTION OF THE DRAWINGS

The invention will be better understood upon reading the following Detailed Description in conjunction with the drawing in which.

DETAILED DESCRIPTION

A preferred embodiment of the novel scenting nebulizer 115 is shown in the Figures for the distribution by nebulization of scented oil and utilizing the novel capacitive liquid level sensor to monitor the level of scenting oil in a bottle 203 of the scenting nebulizer 115. This level sensing is done without contacting the scenting oil, and also provides an appropriate oil level indication that is continuously monitored and used to prevent running out of scenting oil.

Figure 1:
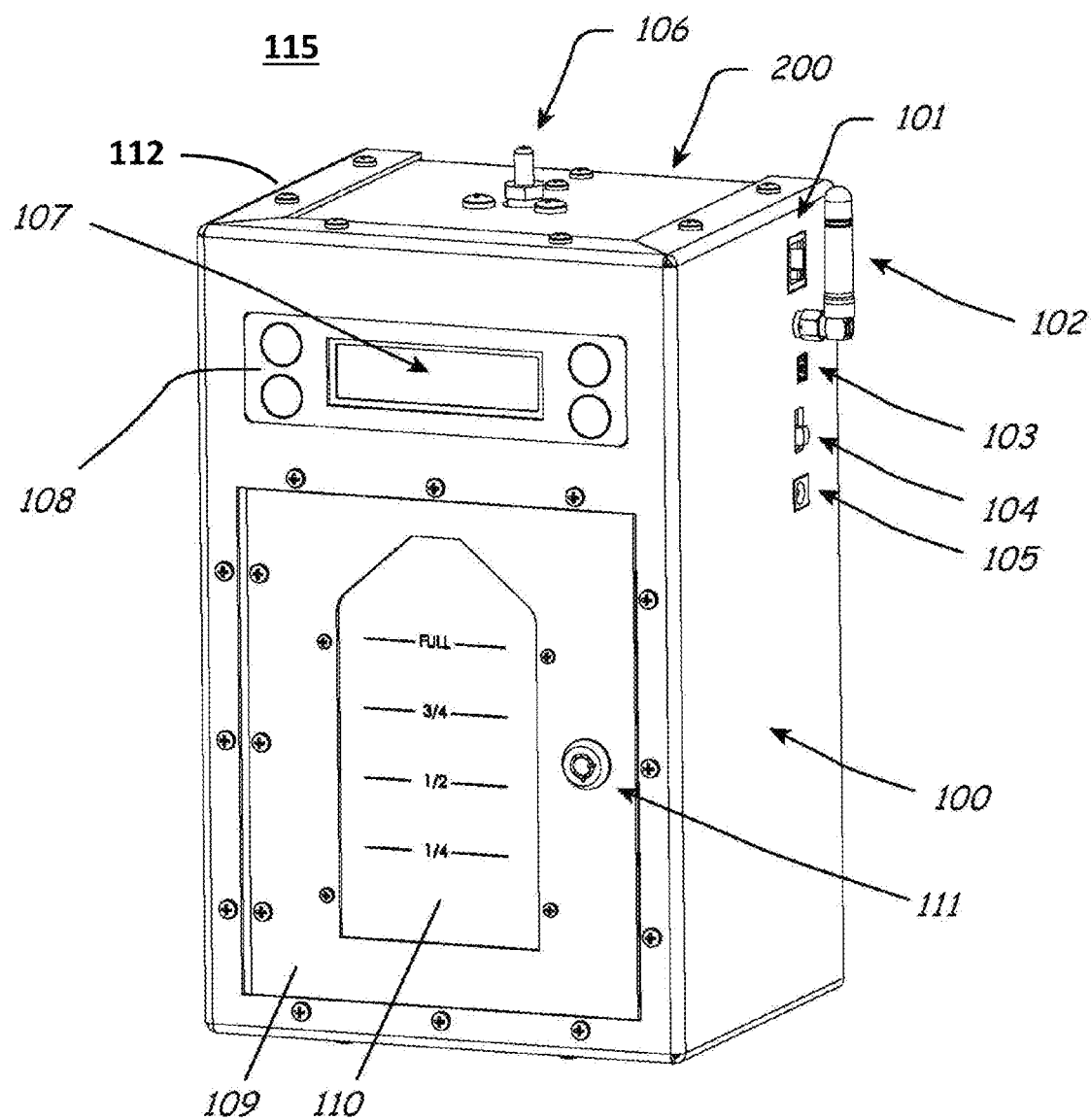
FIG. 1 is a front perspective view of the novel scenting nebulizer.
Figure 4:
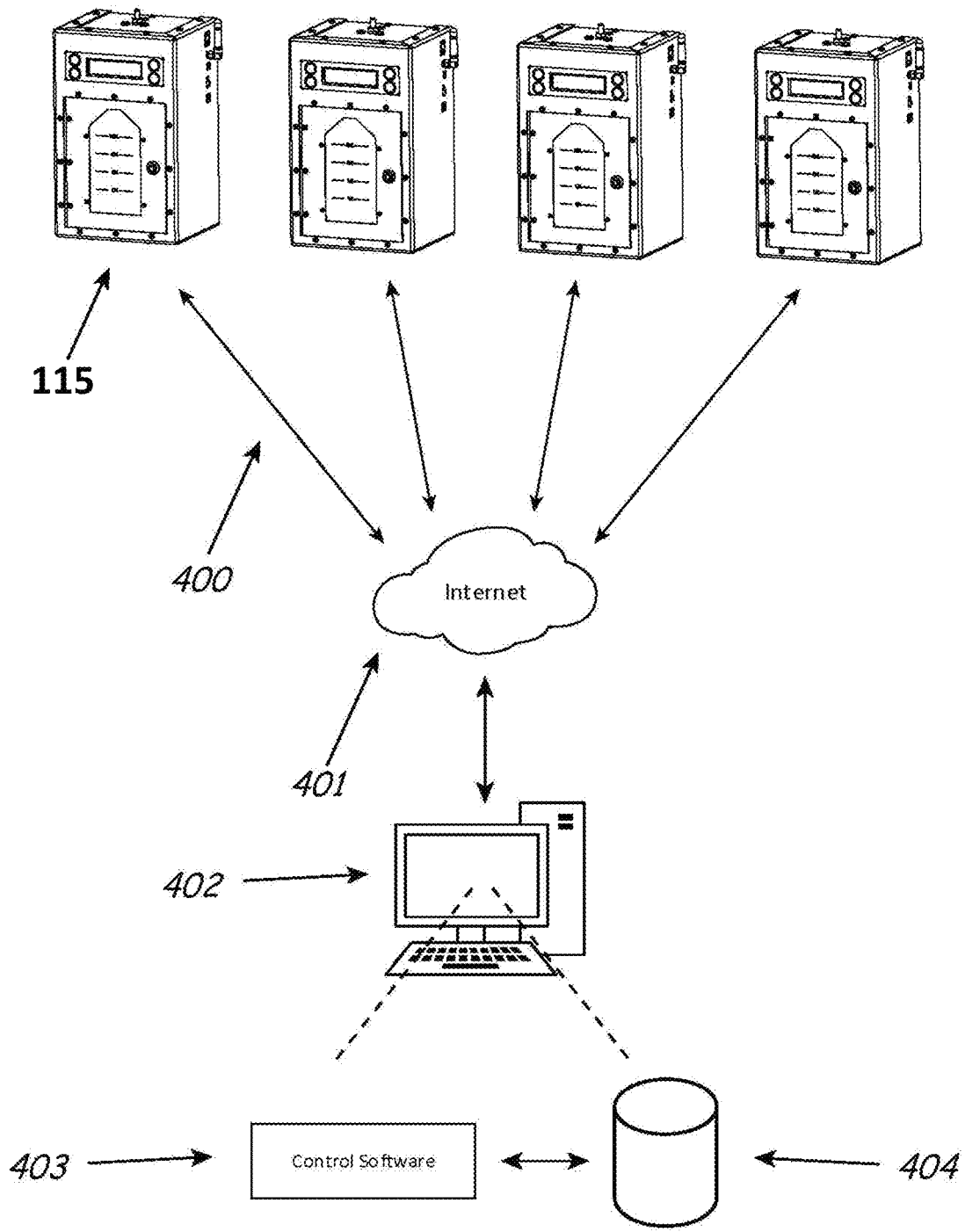
FIG. 4 is a network diagram of a plurality of scenting nebulizers connected to a central computer via wired and wireless local area networks and/or the Internet.

Referring to FIG. 1, the outer construction of scenting nebulizer 115 consists of a top or front cover 100 and a base housing 200, both made of metal with a special chemically resistant powder coating. Top cover 100 is removed from bottom 200 by removing screws 112 such as those shown through the edges of top cover 100 as shown in FIG. 1. Localized user programming of the operation of a scenting device 115 is accomplished by using a membrane keyboard 108 and an LCD display 107. Display 107 may also be used to display information about the rate at which nebulized scenting oil is being dispensed from the scenting nebulizer 115 and other pertinent information. A hinged door 109 is secured with a lock 111 and allows internal access by maintenance personnel. Scenting oil fluid level can be seen though the clear plastic window 110. A clear plastic bottle of scenting oil is mounted inside nebulizer 115 right behind door 109. Connections to scenting nebulizer 115 consist of (1) a conventional wired LAN connector 101 for connecting a scenting nebulizer 115 to a local area network in a building or a group of buildings or connecting the scenting nebulizer 115 to the Internet via a LAN cable as shown in FIG. 4 for remote monitoring and control of nebulizer 150, (2) an antenna 102 for wireless connection of a scenting nebulizer 115 to the local area network in a building or a group of buildings or connect the scenting nebulizer 115 to a wireless router for connection to the Internet, (3) a 2-pin connector 103 for input control, (4) a power switch 104 to turn the unit on and off, and a power jack 105 for connecting an external power supply other than hardwiring power to nebulizer 115. The scenting nebulizer 115 may have an internal battery or an internal power supply wired to AC power. A nebulized oil output barb 106 is connected to a short tube (not shown) to feed nebulized scenting oil into an HVAC system for distribution, or feeding the nebulized scenting oil directly into a room.

Figure 2:
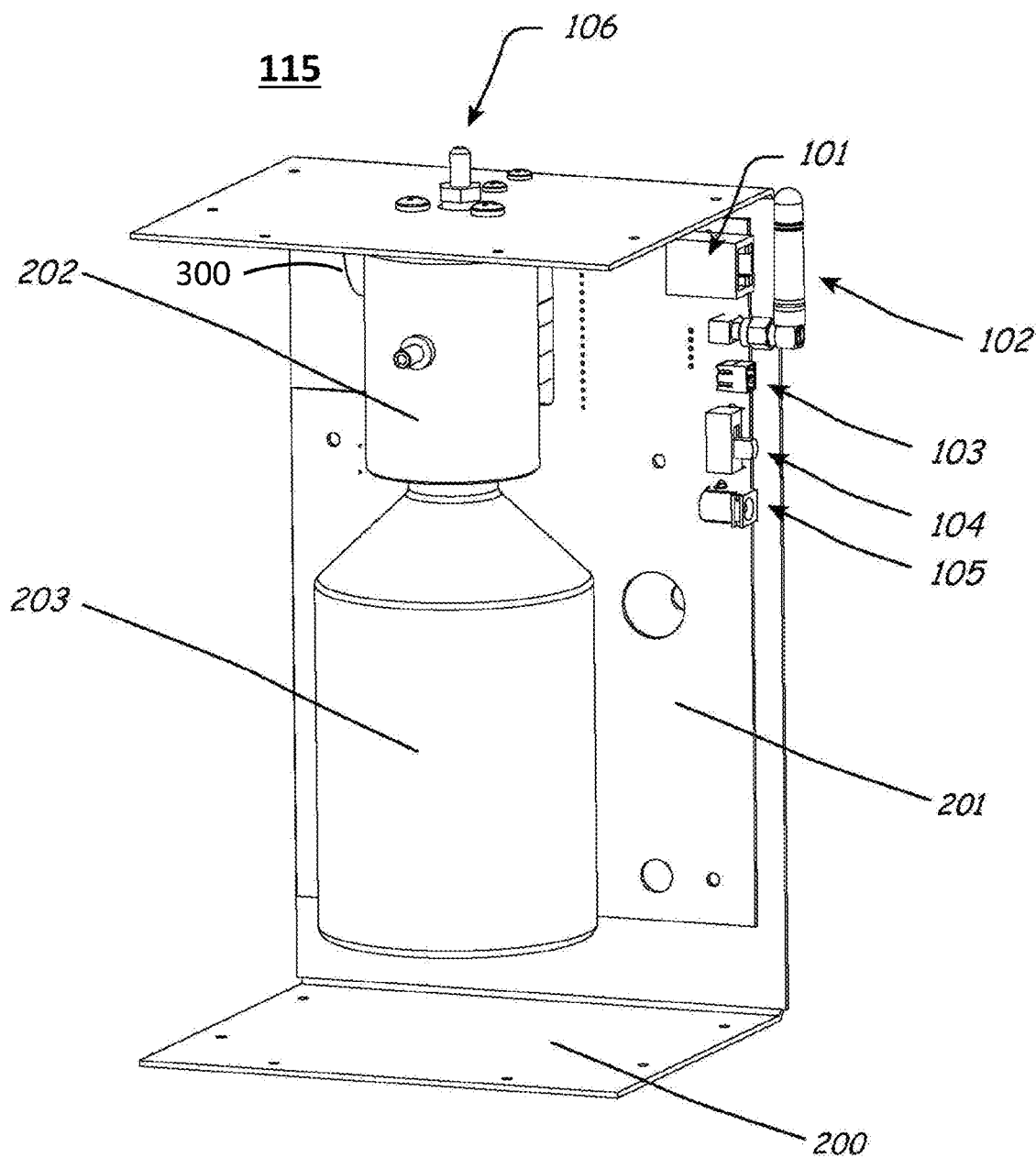
FIG. 2 is a perspective view of the novel scenting nebulizer without its cover.

The scenting nebulizer 115 of the preferred embodiment of the invention utilizes a pressurized air pumping system as shown in FIG. 2 for the nebulization and distribution of scented oil in clear plastic bottle 203. The integrated electronics section consists of a printed circuit card 201 that is mounted to the bottom metal work 200. Connections consist of a wired LAN connector 101, an antenna 102 for wireless connection to the internet, a 2-pin connector 103 for input control, a power switch 104 to turn the unit on and off, and a power jack 105 for connecting an external power as described in the previous paragraph as previously described with reference to FIG. 1. The scenting oil bottle 203 attaches to a nebulizer mechanism 202 by a threaded connection (not shown). Nebulizer 202 includes an air pump 300 for providing pressurized air into scenting oil bottle 203. The pressurized air forces scenting oil out of bottle 203 which is nebulized by nebulizer 202 in a manner well known in the art. The nebulized oil is expelled out of hollow output barb 106 to be distributed into the immediate surrounding area as desired by an operator of the system. Alternatively, the nebulized oil output at barb 106 is input to a hose connected to barb 106 and the nebulized oil is fed into the duct work of a central air-conditioning and heating system (not shown). Scenting oil bottle 203 is preferably round and one attaches to nebulizer 202 by being threaded thereon. However, bottle 203 may have a square or rectangular cross-section and may be fastened to nebulizer 202 in a different way.

Figure 3:
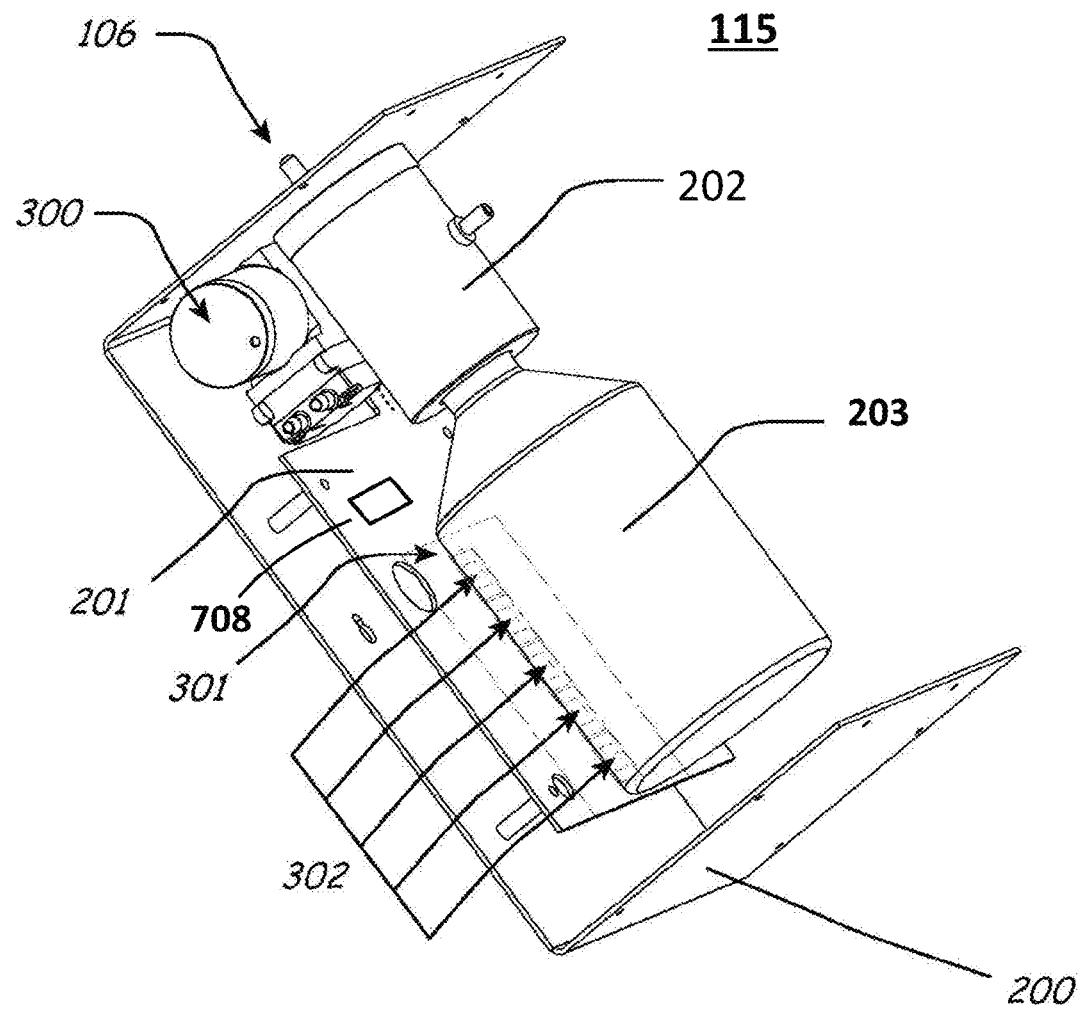
FIG. 3 is a side perspective view of the novel scenting nebulizer and its capacitive oil level sensor pads.

As shown in FIG. 3, the scenting nebulizer 115 of the preferred embodiment of the invention comprises a printed circuit card 201 with a specialized microprocessor 708 thereon and a capacitive scenting oil level sensory array 302. Capacitive level sensor array 302 is shown and described in greater detail with reference to FIG. 6. Sensor array 302 is connected to a specialized microprocessor 708 and the two components provide multi-channel capacitive oil level sensing and oil level reporting to display 107 (FIG. 1) and to a remote central computer 402 (FIG. 4). The printed circuit card 201 is attached to the bottom housing 200 using stand-offs as shown. On the printed circuit card 201 are etched copper pads and guard rings 301 that are part of capacitive sensor array 302 which are shown in and described in greater detail with reference to FIG. 6. The air pump 300 feeds high pressure air into the scenting nebulizer 202 that pressurizes scenting oil bottle 203. The air pressure causes scenting oil exiting bottle 203 to be nebulized in a manner known in the art and the nebulized oil is output from the scenting nebulizer at oil output barb 106. The nebulized oil is input directly to a room or via a hose into the duct work of an HVAC system.

FIG. 4 is a block diagram showing a configuration in which a network of scenting nebulizers 115 are connected by either: (1) a wired or wireless local area network 400 to a centralized computer for 402, or (2) via the Internet 401 to centralized computer 402. The scenting nebulizers 115 may all be located in one location, or may be spread out over many locations across a city, across a state or across a country. The scenting nebulizers 115 are connected via a wired or wireless LAN 400 to central computer 402 (not shown) or LAN 400 may be connected via Internet 401 to central computer 402.

Central computer 402 operates under the control of control software 403 which is stored in a storage device 404 along with scented oil level readings periodically received from all the scenting nebulizers 115. Other operational information about the individual scenting nebulizers 115 is also stored in storage device 404, along with any error information received from any of the nebulizers 150. That is, central computer 402 is used to manage a network of a plurality of scenting nebulizers 115 on a one-to-one basis, all at the same time. The scenting nebulizers 115 are controlled by central computer 402 running the control software 403 in storage device 404. More particularly, using central computer 402 scenting schedule changes, date/time updates, scenting scheduling etc. may be made to individual scenting nebulizers 115. In addition, operational software updates and firmware updates may be made to specific ones of the individual scenting nebulizers 115. The control software 403 stores all scenting units 100 telemetry in a database 404 format.

Figure 5:
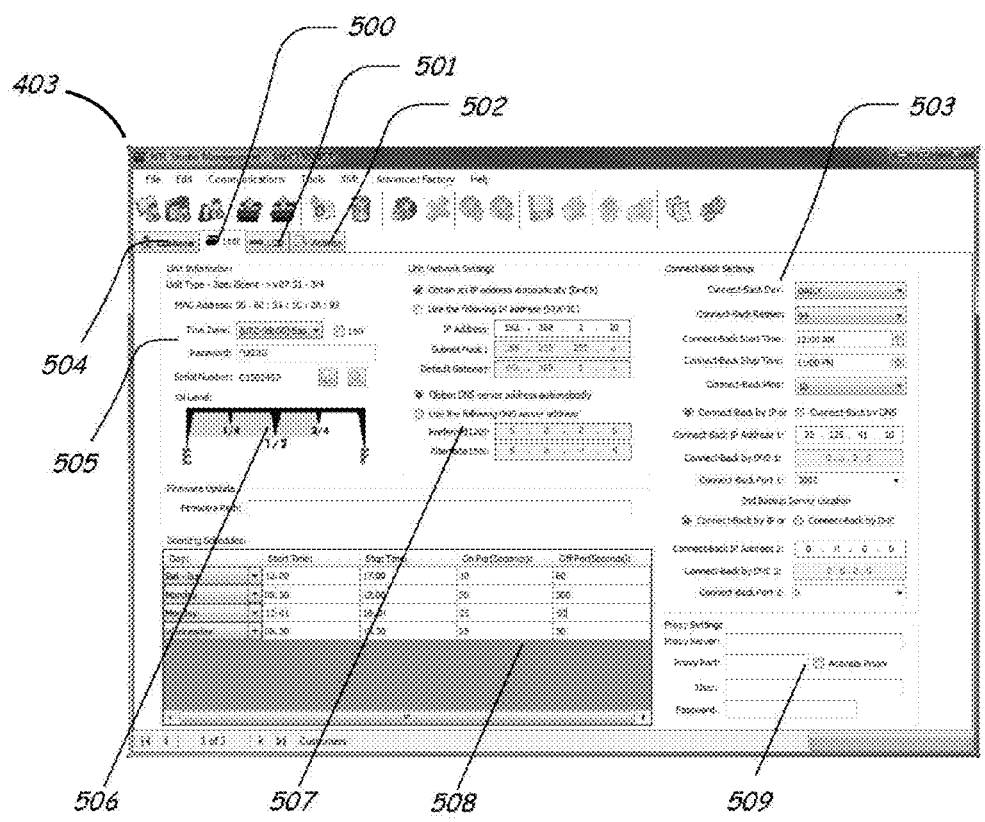
FIG. 5 is a computer screen example of the control software running at the central computer.

Control software 403 running on computer 402 generates a control display interface such as shown in FIG. 5. The display consists of display fields that display stored operational information about each of the plurality of scenting nebulizers 115 connected to computer 402 via the previously described network. The display fields include Customer Tab 504, LCD Tab 501 and Activity Tab 502. The Unit Tab 500 is the main software control interface that has sections that control Unit Information 505, display remote Oil Level 506, Unit Network Settings 507, Connect-Back Settings 503, Schedules 508 & Proxy Settings 509. Using computer 402 running control software 403 at a central location an operator may monitor and control a number of scenting nebulizers 115 all located within one physical location, or a number of scenting nebulizers 115 distributed throughout a number of remote locations across a city, state or country.

Figure 6:
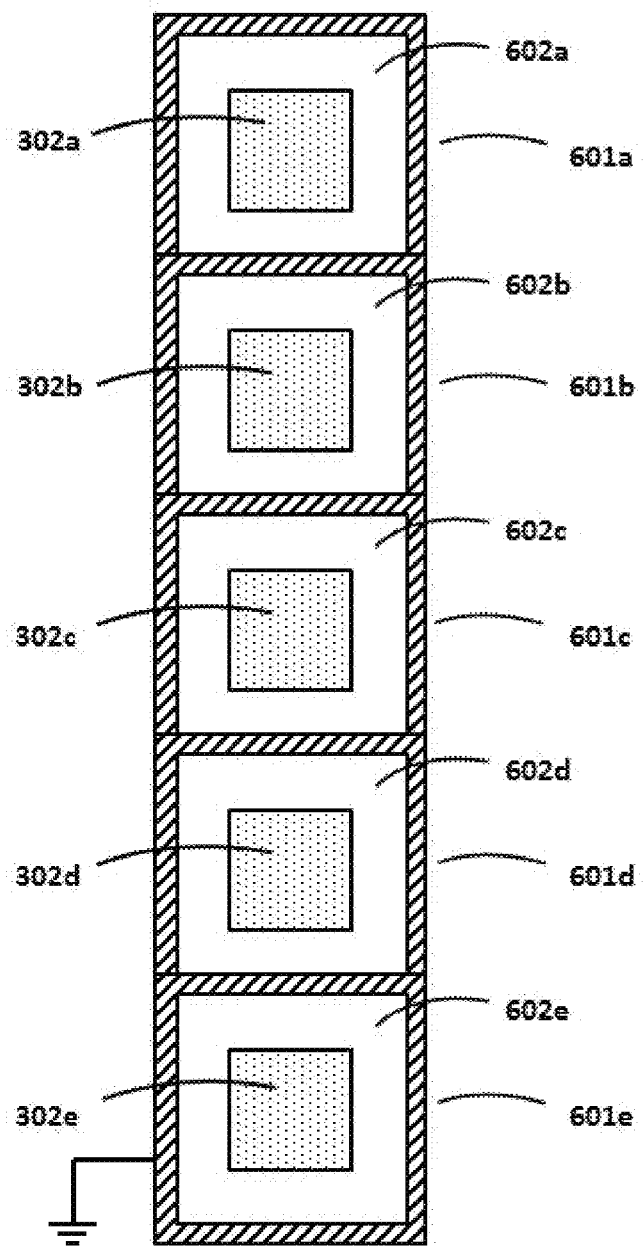
FIG. 6 shows the layout of capacitive level sensor pads used to detect the scenting oil level in a scenting nebulizer.
Figure 7:
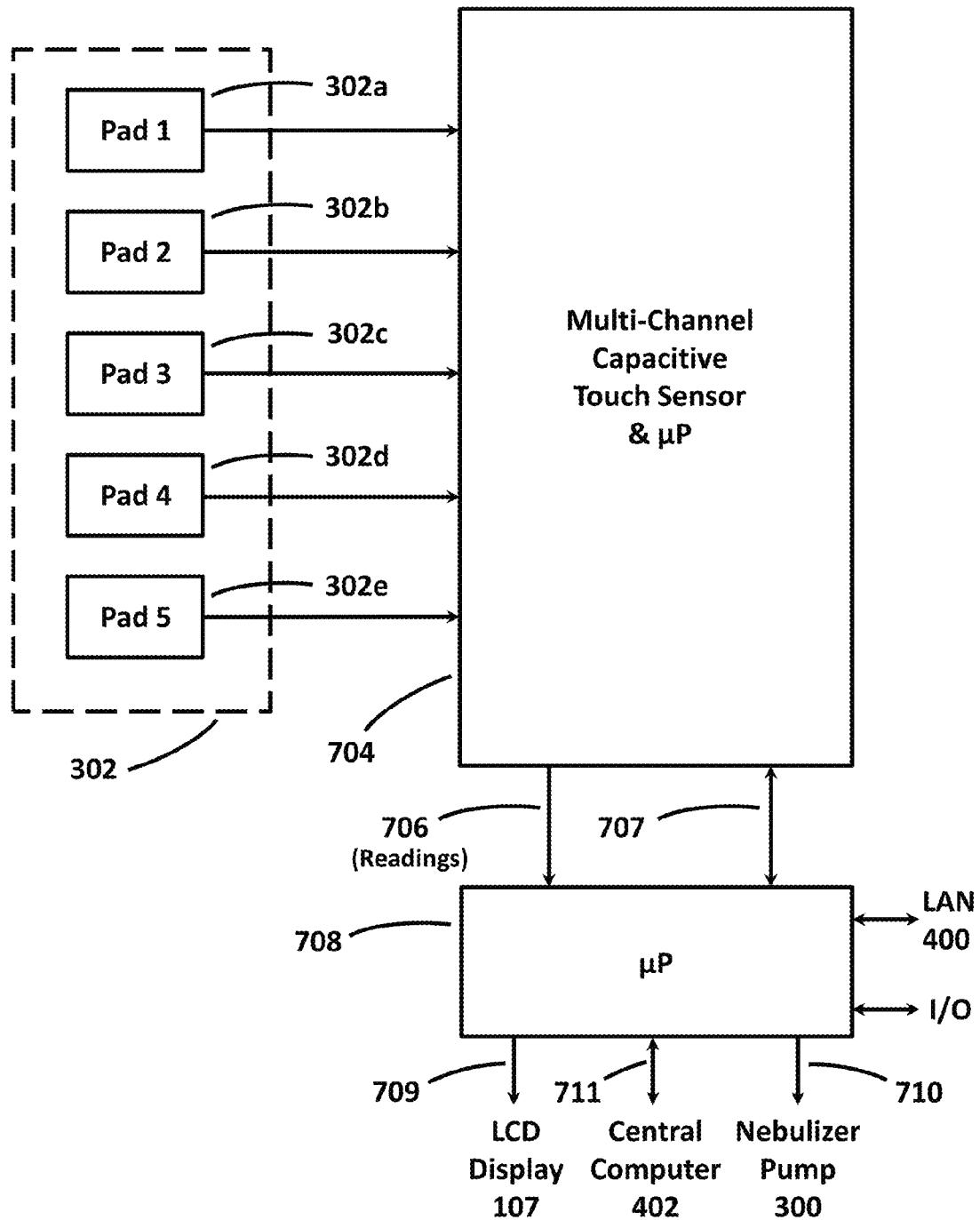
FIG. 7 is a block diagram showing the electronic control of the scenting nebulizer.

In FIG. 6 is shown an enlarged version of the sensor pads 302a-e and guard rings 601a-e shown in and briefly described with reference to FIG. 3. Shown are five sensor pads 302a through 302e that are etched onto printed circuit board 201 (FIGS. 2 and 3) and are used as part of the capacitive liquid level sensing in accordance with the teaching of the invention. Each one of the five sensor pads 302a-e is one plate of a capacitor that makes up a capacitive scenting oil level sensor. These five sensor pads 302a-e are positioned on printed circuit board 201 (FIG. 3) to be closely alongside, and possibly touching, scenting oil bottle 209 as shown in FIG. 3. Each of these etched square copper sensor pads 302a-e is 8 millimeters square and they are center-to-center spaced 18 millimeters from each other as shown. Surrounding each sensor pad 302a-e is an etched square guard wall 601a-e. These guard walls 601 are each 18 millimeters on a side with vertically adjacent sensor pads 302 sharing a common guard wall 601 as shown. The width of the etched guard walls 601 is 0.050 inches. This leaves a space 602 around each of the sensor pads 302. All the guard walls 601 are connected to an electrical ground. The guard walls 601a-e minimize or prevent electrical interference between adjacent sensor pads 302a-e and they also help shape an electric field emanating from each sensor. The purpose of the electric fields is described further in this detailed description. Also not shown in FIG. 6 are etched copper paths or traces that connect all five sensor pads 302a-e to a multi-channel, special purpose capacitive sensor microprocessor 704 as shown in FIG. 7. Specialized microprocessor 704 is a Microchip CAP1298 Capacitive Touch Sensor. However, and most importantly, in the scenting nebulizer 115 microprocessor 704 is not used as a touch sensor.

Over the top of the sensors 302a-e, guard walls 601 and printed circuit board 201 on which the sensors and guard walls are located, is deposited a 0.002 inch thick layer of solder mask. On the printed circuit board 201 on which sensor pads 302 and guard walls 601 are etched there is no copper layer beneath the pads and guards serving as a ground plane.

The guard walls 601a-e are connected to electrical ground to minimize the electric fields generated by any one of the sensor pads 302a-e from interfering with the operation of an adjacent sensor pad as a plate of a capacitive touch sensor.

Referring briefly to FIG. 3, when the bottle 203 of scenting oil is mounted in scenting nebulizer 115 its outer wall touches or is within a few ten thousandths of an inch from sensor pads 302a-e. When in operation, each of sensor pads 302a-e has an electrical potential applied thereto and from each of sensor pads 302a-e emanates an electric field that is described in the next paragraph.

The five capacitors used for the novel capacitive oil level sensing, the capacitance values of which are measured by specialized microprocessor 704, each comprise the following. One of the sensor pads 302a-3 acts as one plate of each of the five capacitors, the housing of scenting nebulizer 115 acts as the other plate of the same capacitor and is common for all five capacitors. The housing at ground potential. The dielectric of each of the five capacitors comprises the layer of solder mask over the associated one of the sensor pads 302, the walls of bottle 203, and the scenting oil in the bottle 203. Thus, there are five capacitors formed. It is the value of each of these five capacitors that is individually measured by specialized microprocessor 704 as a dielectric values changes when the level of the scenting oil in bottle 203 goes down. The electric field generated during operation of each of the five capacitors emanates from each of sensor pads 302*a-e* passes through the layer of solder mask over each sensor pad, through the wall of bottle 203 and through any scenting oil therein and terminates in the housing of scenting nebulizer 115. Accordingly, as the level of the scenting oil in bottle 203 goes down in front of each of the sensor pads 302 the value of the dielectric in front of the pads changes. This changes the value of the capacitor which is measured and capacitive oil level sensing is achieved.

FIG. 7 is an electrical block diagram circuit of a single scenting nebulizer 115 (FIG. 4). Shown are the five sensor pads 302*a-e* (FIG. 6) that are connected to a multi-channel capacitive touch sensor microprocessor 704. Microprocessor 704 is a specialized processor Microchip CAP1298 Capacitive Touch Sensor. However, and very important, in the scenting nebulizer 115 microprocessor 704 is not being used as a touch sensor. Microprocessor 704 measures the value of capacitance of each of five capacitors of each of which one of sensor pads 302*a-e* is a part. Specialized microprocessor 704 is connected to another microprocessor 708 inside the scenting nebulizers 115 and the capacitance values, and any changes therein, are forwarded via leads 706 to microprocessor 708.

Specialized microprocessor 704 (Microchip CAP1298) is programmed to measure the capacitance of each of the five capacitors formed by each of sensor pads 302*a-e* once every second. However, the sampling time rate may be increased. These capacitance readings are forwarded via leads 706 to microprocessor 708. There are two fundamental methods for detecting a shift in capacitance using a microprocessor. The first is to use a voltage measurement where the system manipulates the pin of the sensor, to place a voltage based on the amount of capacitance on the pin, and looks for a shift in the voltage reading on the sensor. This includes methods such as Microchip's Charge Time Measurement Unit (CTMU) and Capacitive Voltage Divider (CVD). The alternative is to measure the sensor using a frequency approach which uses a pseudo-randomized frequency to sense changes in capacitance.

When a full bottle 203 of scenting oil is first installed in a scenting nebulizer 115 the capacitance values measured for each of the five capacitors is averaged and stored as a figure indicating there is the maximum amount of oil in front of each of sensor pads 302*a-e*. The full bottle 203 yields a maximum capacitance measurement for each of the five capacitors and is referred to as "max value" in this description. Similarly, when there is no bottle or an empty bottle 203 positioned in nebulizer 115 it yields a minimum capacitance measurement for each of the five capacitors and is referred to as "min value" in this description.

As the scenting oil in bottle 203 is used up the level of scenting oil in bottle 203 goes down. When this happens, the amount of scenting oil in bottle 203 in front of each of the sensor pads 302 decreases, starting with the uppermost sensor pad 302*a* and going to the lowermost sensor pad 302*e*. That is, as the scenting oil is used up, there is sequentially no scenting oil in front of the capacitors utilizing sensor pads 302*a-e*. Thus, the value of the dielectric in front of each of the five capacitors sequentially changes and the change is sensed by the specialized microprocessor 704 that is periodically measuring the capacitance of each of the five capacitors. In actual operation of a scenting nebulizer 115 the capacitance values determined every second by microprocessor 704 are forwarded via leads 706 to microprocessor 708. Microprocessor 708 takes these capacitance readings for each of the five capacitors received over a small finite time period and averages them to calculate a capacitance reading that is stored. Each sequentially stored average capacitance reading is compared to the initially stored max value and min value capacitance figures and microprocessor 708 can then determine which of the five sensor pads 302*a-e* the scenting oil level is in front of. Microprocessor 708 also uses the stored max value and min value capacitance figures and interpolates an actual averaged, stored capacitance figure between these two values to mathematically determine the actual level of the scenting oil in front of a sensor pad 302.

Thus, as the level of scenting oil in bottle 203 goes down microprocessor 708 mathematically determines by interpolation that there is no scenting oil in front of the uppermost capacitor of which sensor pad 302*a* is part. This interpolation process is sequentially repeated for each of sensor pads 302*b-e* as microprocessor 708 mathematically determines by interpolation the actual level of the scenting oil in front of a sensor pad 302*b-e*.

Microprocessor 708 also interacts with specialized microprocessor 704 via control signals on leads 707. These control signals indicate to microprocessor 704 how often the level of the scenting oil in bottle 203 should be capacitively measured and the level reading returned to microprocessor 708. Further, microprocessor 708 provides display output signals to LCD display 107 via leads 709, provides control signals to operate nebulizer air pump 300 via leads 710, and receives control signals from keyboard buttons 108 on the front of each scenting nebulizer 115 via leads 711.

In the networked configuration of scenting nebulizers 115 shown in FIG. 4 microprocessor 708 in each of scenting units 115 forward their calculated scenting oil level readings via LAN leads 400 to remote processor 402 as described with reference to FIG. 4. Remote processor 402 utilizes these scented oil level readings to initiate maintenance action to replace an almost empty bottle 203 of scenting oil before it is fully emptied.

When a scenting nebulizer 115 is operating in a standalone manner local microprocessor 708 will initiate appropriate visual warnings/readings on display 107 (FIG. 1) of a scenting nebulizer 115, and provide an audible signal when the level of the scenting oil gets too low.

While what has been described herein is a preferred embodiment of the invention those skilled in the art will recognize that numerous changes may be made without departing from the spirit and scope of the invention. More particularly, while the preferred embodiment of the invention described herein is used to measure the level of scenting oil in a scenting nebulizer the novel capacitive liquid level sensing may be utilized to measure the level of any type of liquid in a non-conductive container. In addition,

The invention claimed is:
1. A circuit for capacitively sensing the level of scenting oil in a non-conductive container mounted inside a case of a scenting nebulizer without physically contacting the scenting oil, the circuit comprising:
   a plurality of first electrodes being arranged one above the other inside the nebulizer, and each of the plurality of first electrodes being at a first electrical potential;

a second electrode being spaced from the plurality of first conductive electrodes, the second electrode being the case of the scenting nebulizer and the case being at a second electrical potential;

wherein each of the plurality of first electrodes and the second electrode form a like plurality of capacitors whose capacitance value is to be measured and used to sense the level of scenting oil in the container, wherein the non-conductive container having the scenting oil therein is positioned between the plurality of first electrodes and the second electrode, and the non-conductive container and scenting oil therein is between the plurality of first electrodes and the second electrode and act as a dielectric for each of the like plurality of capacitors formed by the electrodes, and wherein when the non-conductive container is full of scenting oil the measured capacitance of each of the like plurality of capacitors formed by the plurality of first electrodes and the second electrode is at a maximum capacitance reading, and when the level of the scenting oil in the non-conductive container acting as a dielectric for ones of the plurality of capacitors decreases the measured capacitance of the last mentioned capacitors decreases and gives an indication of the decreased level of sensing oil.

2. The circuit for capacitively sensing the level of scenting oil in a non-conductive container of claim 1 further comprising a guard, the guard being formed of copper, the guard surrounding each of the plurality of first electrodes, the guards being electrically grounded and shielding each of the first plurality of electrodes from interference caused by adjacent ones of the first plurality of electrodes.

3. The circuit for capacitively sensing the level of scenting oil in a non-conductive container of claim 1 further comprising a programmed microprocessor that has plural inputs with one input being connected to each of the plurality of first electrodes and each of the first electrodes is part of one of the like plurality of capacitors, the microprocessor repeatedly measuring the capacitance of each of the last mentioned capacitors during known sequential periods of time, the microprocessor averaging the capacitances measured during each period of time to get a calculated capacitance value for each time period for each capacitor, and the microprocessor using the calculated capacitance values for each period of time for each of the capacitors to determine the level of the scenting oil in the non-conductive container.

4. The circuit for capacitively sensing the level of scenting oil in a non-conductive container of claim 3 further comprising:

first means for measuring a maximum calculated capacitance of each of the capacitors formed using the plurality of first electrodes when the container is full of scenting oil, and for measuring a minimum calculated capacitance of each of the same capacitors when there is no container or the container is empty of scenting oil;

second means for interpolating each of the calculated capacitance values for each periodic time period for each of the plurality of capacitors against the maximum calculated capacitance and the minimum calculated capacitance for each of the plurality of capacitors to determine the level of scenting oil in the non-conductive container.

5. The circuit for capacitively sensing the level of scenting oil in a non-conductive container of claim 4 further comprising a guard on the printed circuit board, the guard being formed of copper on the printed circuit board, the guard surrounding each of the plurality of first electrodes, the guards being electrically grounded and shielding each of the first plurality of electrodes from interference caused by adjacent ones of the first plurality of electrodes.

\* \* \* \* \*